US007144430B2

(12) United States Patent
Archer et al.

(10) Patent No.: US 7,144,430 B2
(45) Date of Patent: Dec. 5, 2006

(54) WRIST DEVICE FOR USE WITH A PROSTHETIC LIMB

(75) Inventors: Shawn L. Archer, Salt Lake City, UT (US); Arthur D. Dyck, Draper, UT (US); Reed H. Grant, Salt Lake City, UT (US); Edwin K. Iversen, Salt Lake City, UT (US); Steve R. Kunz, Salt Lake City, UT (US); James R. Linder, West Jordan, UT (US); Harold H. Sears, Salt Lake City, UT (US)

(73) Assignee: Motion Control, Inc., Salt Lake City, UT (US)

( * ) Notice: Subject to any disclaimer, the term of this patent is extended or adjusted under 35 U.S.C. 154(b) by 302 days.

(21) Appl. No.: 10/618,525

(22) Filed: Jul. 11, 2003

(65) Prior Publication Data

US 2004/0015240 A1    Jan. 22, 2004

Related U.S. Application Data

(60) Provisional application No. 60/395,718, filed on Jul. 12, 2002.

(51) Int. Cl.
*A61F 2/58* (2006.01)
*A61F 2/70* (2006.01)

(52) U.S. Cl. .......................................... 623/61; 623/62
(58) Field of Classification Search ............ 623/61–64, 623/47, 57; 403/93, 96, 97, 103; 901/29
See application file for complete search history.

(56) References Cited

U.S. PATENT DOCUMENTS 2,812,961 A * 11/1957 Brown et al. .................. 403/93

* cited by examiner

*Primary Examiner*—David H. Willse
(74) *Attorney, Agent, or Firm*—Thorpe, North & Western LLP

(57) ABSTRACT

A wrist device is provided for use with a prosthetic limb. The wrist device includes a base plate that is configured for attachment to a prosthetic limb and a sliding lock plate that is slidably engaged with the base plate. Both the base plate and the sliding lock plate have openings. Also included in the invention is a semi-cylindrical rotator that is configured for attachment to a prosthetic hand. The semi-cylindrical rotator has slots configured to receive the sliding lock plate and is coupled to the base plate in a manner that allows the sliding lock plate to lock into the slots.

13 Claims, 5 Drawing Sheets

WRIST DEVICE FOR USE WITH A PROSTHETIC LIMB

This application claims priority to U.S. Provisional application 60/395,718 filed on Jul. 12, 2002.

FIELD OF THE INVENTION

The present invention relates generally to wrist devices for use with prosthetic limbs.

BACKGROUND OF THE INVENTION

There are thousands of individuals with absences of arms or hands in the United States alone and thousands of new amputees each year. Many of these amputees are fitted with electrically powered hand and arm prostheses. The utility of an electric hand prosthesis is greatly enhanced by the ability to rotate and flex the hand prosthesis. Once an object is grasped with a prosthetic hand, the object can be oriented for a desired task if the prosthesis can rotate and flex. A below the elbow amputee usually has four degrees of freedom available, which are humeral flexion/extension, abduction/adduction, rotation and elbow flexion. To orient an object into an arbitrary orientation, two or more degrees of freedom are essential. Also, simple tasks like holding a fork or a tray of food in the needed orientation are difficult to do without wrist flexion/extension.

Wrist rotation and wrist flexion allow the amputee to better orient grasped objects. Wrist rotation alone is not enough to provide this flexibility that most prosthesis users desire. However, currently available wrist flexion devices are heavy, long, and are not easily locked in position. Currently available wrist rotators and flexion devices can add several inches of length and several ounces of weight, making the prosthesis awkward and cumbersome. Some known rotators can add about 2.5 inches and 3.5 ounces to the weight of the prosthesis. Adding a wrist flexion device that is currently commercially available can add another 1 or 2 inches and 2 or 3 ounces. This means an addition of approximately 4 inches and 6 ounces to get both rotation and flexion. Four inches in the wrist area is too long for most amputees to use with ease, especially amputees who have retained most of their forearm. For this reason, few amputees utilize two or three degree-of-freedom wrists. This generally limits the usefulness of the prosthesis.

SUMMARY OF THE INVENTION

The present invention provides a wrist device for use with a prosthetic limb. The wrist device includes a base plate that is configured for attachment to a prosthetic limb and a sliding lock plate that is slidably engaged with the base plate. Both the base plate and the sliding lock plate have openings. Also included in the invention is a semi-cylindrical rotator that is configured for attachment to a prosthetic hand. The semi-cylindrical rotator has slots configured to receive the sliding lock plate and is coupled to the base plate in a manner that allows the sliding lock plate to lock into the slots. In one embodiment of the invention torsional springs can be positioned such that the wrist can allow the prosthetic hand to center itself within its range of motion and exhibit spring impedance to flexion and extension.

DETAILED DESCRIPTION

Figure 1:
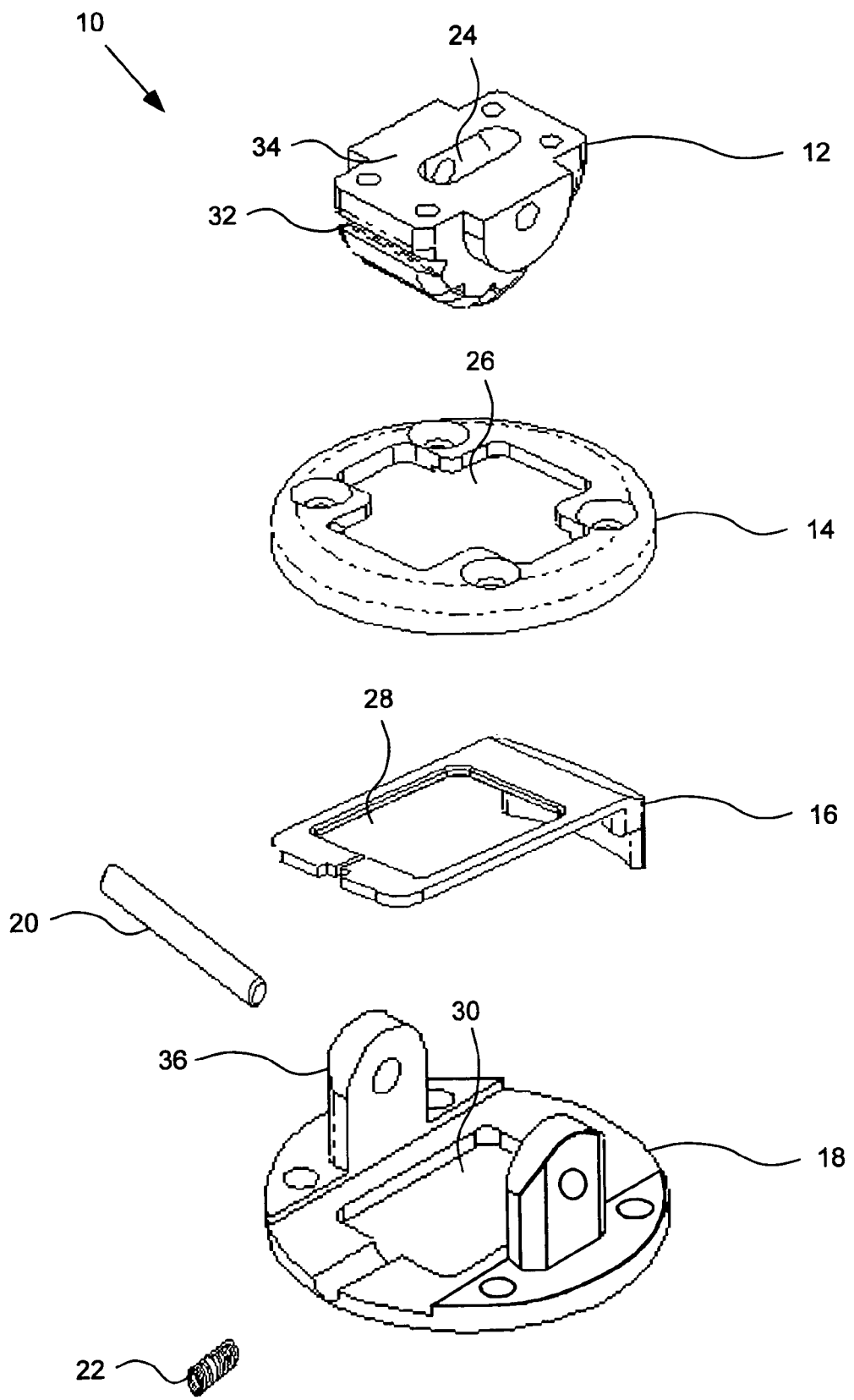
FIG. 1 is a perspective view of a wrist device in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention provides a wrist device for use with a prosthetic limb. The wrist device of the present invention can provide many advantages for amputees because the wrist device is lightweight and compact relative to the wrist devices presently available. For example, the wrist device includes a semi-cylindrical rotator that allows the wrist to exhibit compliance in flexion and extension directions while adding relatively little length and weight to the device. The utility of the wrist device is further increased by a sliding lock mechanism that does not add a significant amount of weight or length to the device. An amputee can lock the wrist device in a desired position with the sliding lock mechanism, which helps the amputee in using a mechanical hand to grasp objects.

As shown in FIG. 1, the wrist device 10 includes a base plate 18 with an opening 30. The base plate is configured to be connected to a prosthetic limb, such as a prosthetic arm. A semi-cylindrical rotator 12 gives the wrist the ability to rotate in a flexion or extension direction. A top portion 34 of the semi-cylindrical rotator is configured for connection to a prosthetic hand. The cylindrical portion of the rotator has a plurality of slots 32 that are configured to receive a sliding lock plate 16. The sliding lock plate is slidably engaged with the base plate in order to lock into the slots of the semi-cylindrical rotator. The sliding lock plate also includes an opening 28. In one embodiment of the invention, the sliding lock plate is coupled to the base plate so that the sliding lock plate's opening is aligned with the base plate's opening in a manner that allows the semi-cylindrical rotator to at least partially pass through the base plate and the sliding lock plate. The opening in the base plate can be in a central portion of the base plate, and the opening in the sliding lock plate can be in a central portion of the sliding lock plate, according to one embodiment of the invention.

The relatively short height of the present invention can be achieved in part by utilizing a sliding lock plate that is thin relative to the locking pins or clamping balls that have been used in the past. Although the sliding lock plate is relatively thin, the sliding lock plate is still strong enough to be used effectively and safely in the wrist device. The strength of the locking device is maximized by minimizing the gap between the semi-cylindrical rotator and the base plate. Furthermore, the portion of the sliding lock plate that comes in contact with the semi-cylindrical rotator can be made to extend the full width of the wrist, which provides additional locking strength.

In one embodiment of the invention, a cover plate 14 with an opening 26 is coupled to the base plate 18 over the sliding lock plate 16 in a manner that limits movement of the sliding lock plate to sliding between the base plate and cover plate. In another embodiment, the base plate is configured to limit movement of the sliding lock plate so that the sliding lock plate always remains flush against the base plate.

The semi-cylindrical rotator is coupled to the base plate in a manner that allows the rotator to rotate around an axis. This can be accomplished by configuring the base plate to include two supporting arms 36 with holes that can receive a pivot pin 20. The pivot pin is coupled to these supporting arms and passes through a hole in the semi-cylindrical rotator 12. In a different embodiment, instead of having supporting arms, the base plate can be configured to directly receive the pivot pin. When the invention includes a cover plate 14, the cover plate can also be configured to receive the pivot pin in a manner that would allow the semi-cylindrical rotator to turn. Alternatively, the cover plate and the base plate can be configured to allow the pivot pin to sit between them.

A primary latch return spring can be connected to the base plate and to the sliding lock plate. The spring presses against the sliding lock plate and biases the sliding lock plate in a locked position. In the locked position, the sliding lock plate is engaged with the semi-cylindrical rotator to prevent the semi-cylindrical rotator from rotating. When an amputee presses on the sliding lock plate, the plate can disengage from the slots in the semi-cylindrical rotator and allow the semi-cylindrical rotator the freedom to rotate.

The opening in the base plate and the opening in the sliding lock plate allow for a minimization of the height of the device. The semi-cylindrical rotator can pass at least partially through the opening in the base plate and the opening in the sliding lock plate. This allows the height of the wrist device to be minimized because the rotator's full height is not added to the height of the device. When the wrist device uses a cover plate, the semi-cylindrical rotator can be coupled to the base plate so that the semi-cylindrical rotator passes through the opening in the cover plate. When configured in this manner, the height of the wrist device is small enough to make the wrist device useful for practically any amputees desiring to use a mechanical hand.

Figure 2:
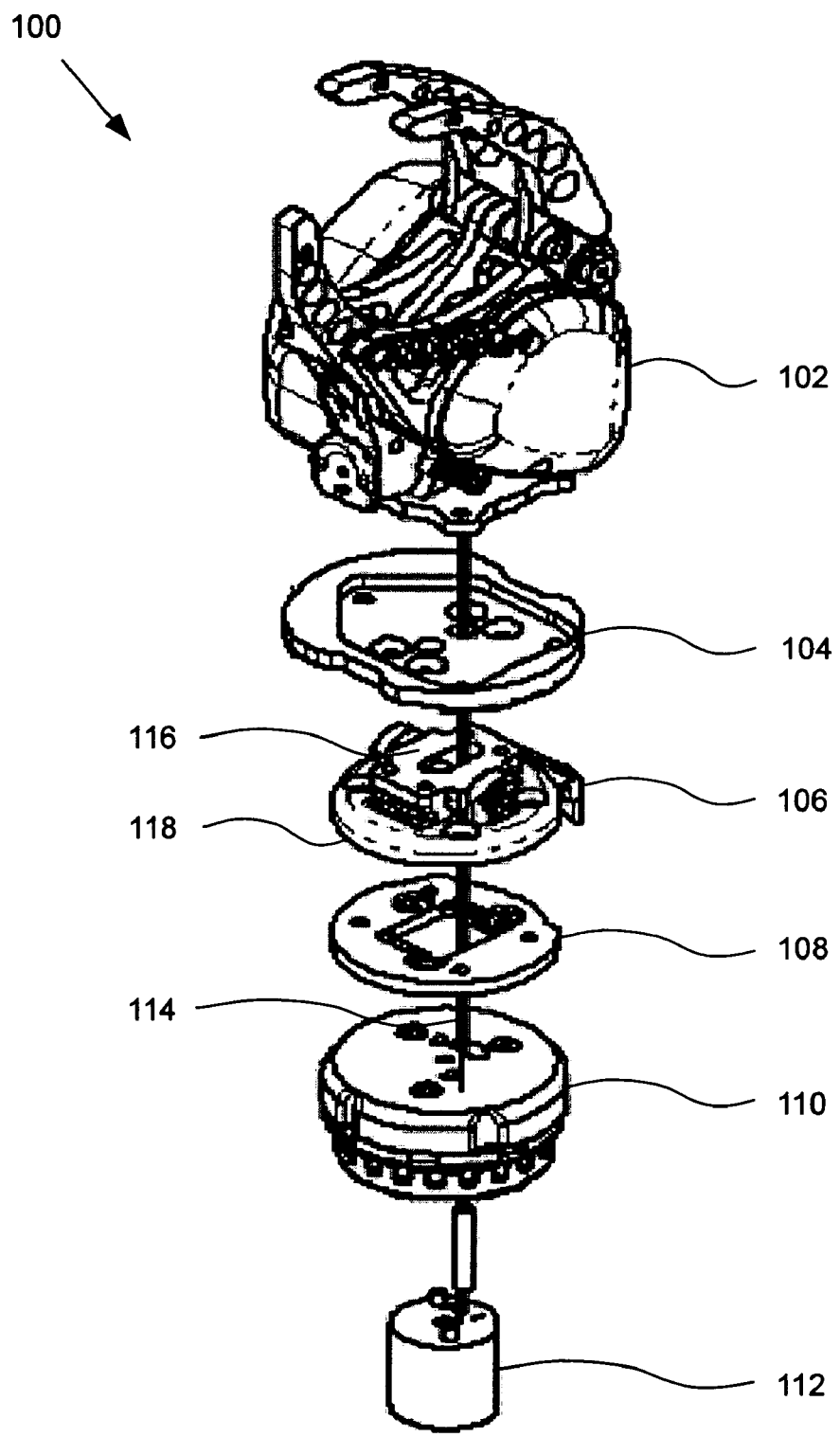
FIG. 2 is a perspective view of a prosthetic hand device according to an embodiment of the present invention.

The prosthetic wrist device can be included as part of a prosthetic arm device 100, as shown in FIG. 2. The prosthetic wrist includes a base plate 118 and a sliding lock plate 106 coupled to the base plate. As previously mentioned, a semi-cylindrical rotator 116 with slots is coupled to the base plate so that the sliding lock plate will lock into the slots of the semi-cylindrical rotator. A lower mounting plate 108 is coupled to the base plate. A wrist quick disconnect unit 110 is coupled to the lower mounting plate, and an upper mounting plate 104 is coupled to the semi-cylindrical rotator. The prosthetic wrist device also includes a prosthetic hand 102 that is coupled to the upper mounting plate. Additionally, a coax connector 112 can be coupled to the wrist quick disconnect unit.

A bundle of wires 114 is coupled to the coax connector and routed through the wrist disconnect unit, the lower mounting plate, the base plate, the sliding lock mechanism, the semi-cylindrical rotator, and the upper mounting plate. The bundle of wires is then coupled to the prosthetic hand so that it can carry control signals to the hand.

Figure 3:
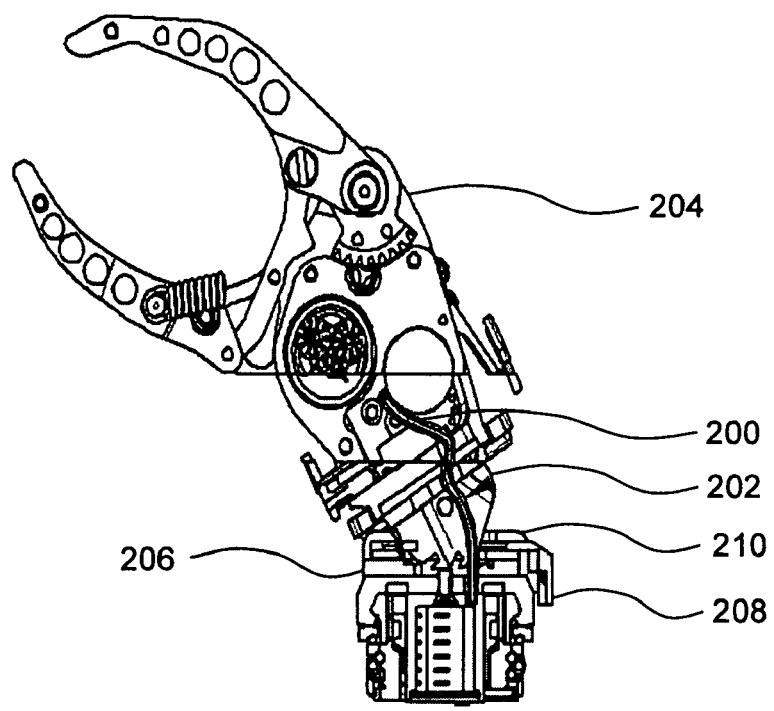
FIG. 3 is a cross sectional view of an embodiment of the invention for a prosthetic device with flexion and extension movement.

FIG. 3 shows a cross sectional view of wires routed through the wrist device. The prosthetic hand 204 attached to the semi-cylindrical rotator 202 can be a mechanical hand that receives electrical control signals. The wires 200 can be routed through the opening in the base plate 206, the opening in the sliding lock plate 208, the opening in the cover plate 210, and the opening in the central portion of the semi-cylindrical rotator. The wires can be routed through the rotator in such a way as to allow the wires to travel close to the neutral axis. This ensures that the wires are minimally stressed and at the same time protected from being snagged or crushed by contact with the environment. This may include wrapping the wires around the neutral axis to reduce the effect of repetitive flexing on the wires. Multi-strand wires can also be used because they tolerate repetitive flexing better than single strand wires.

Figure 4:
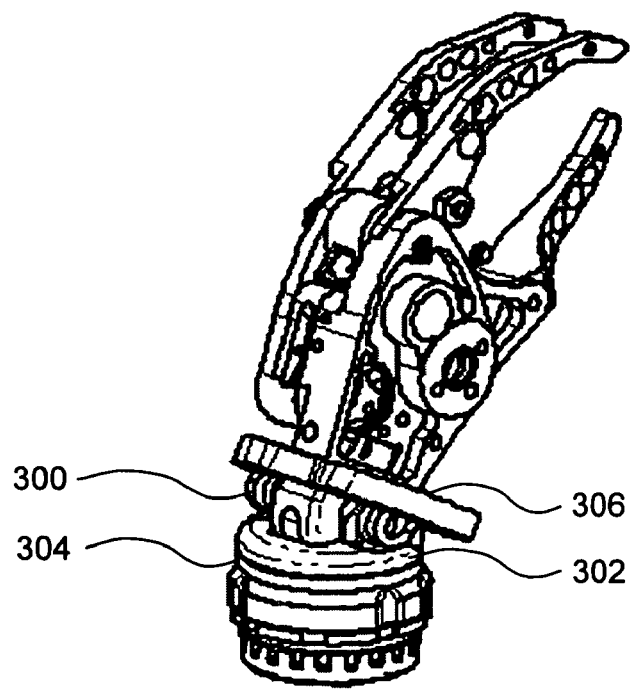
FIG. 4 is a perspective view of an embodiment of the present invention for a prosthetic device with flexion and extension movement.
Figure 5:
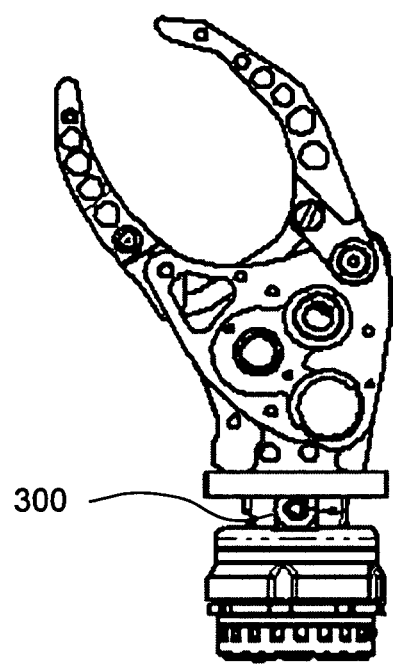
FIG. 5 is a side view of an embodiment of the invention for a prosthetic device with flexion and extension.
Figure 6:
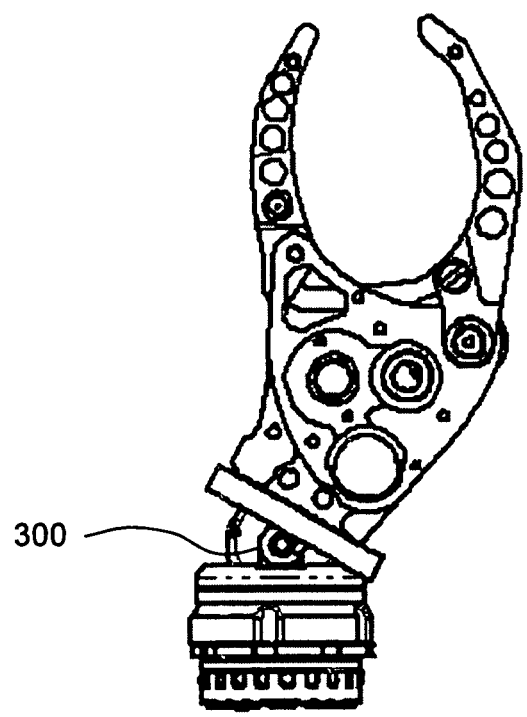
FIG. 6 is a side view of an embodiment of the invention for a prosthetic device with flexion and extension.
Figure 7:
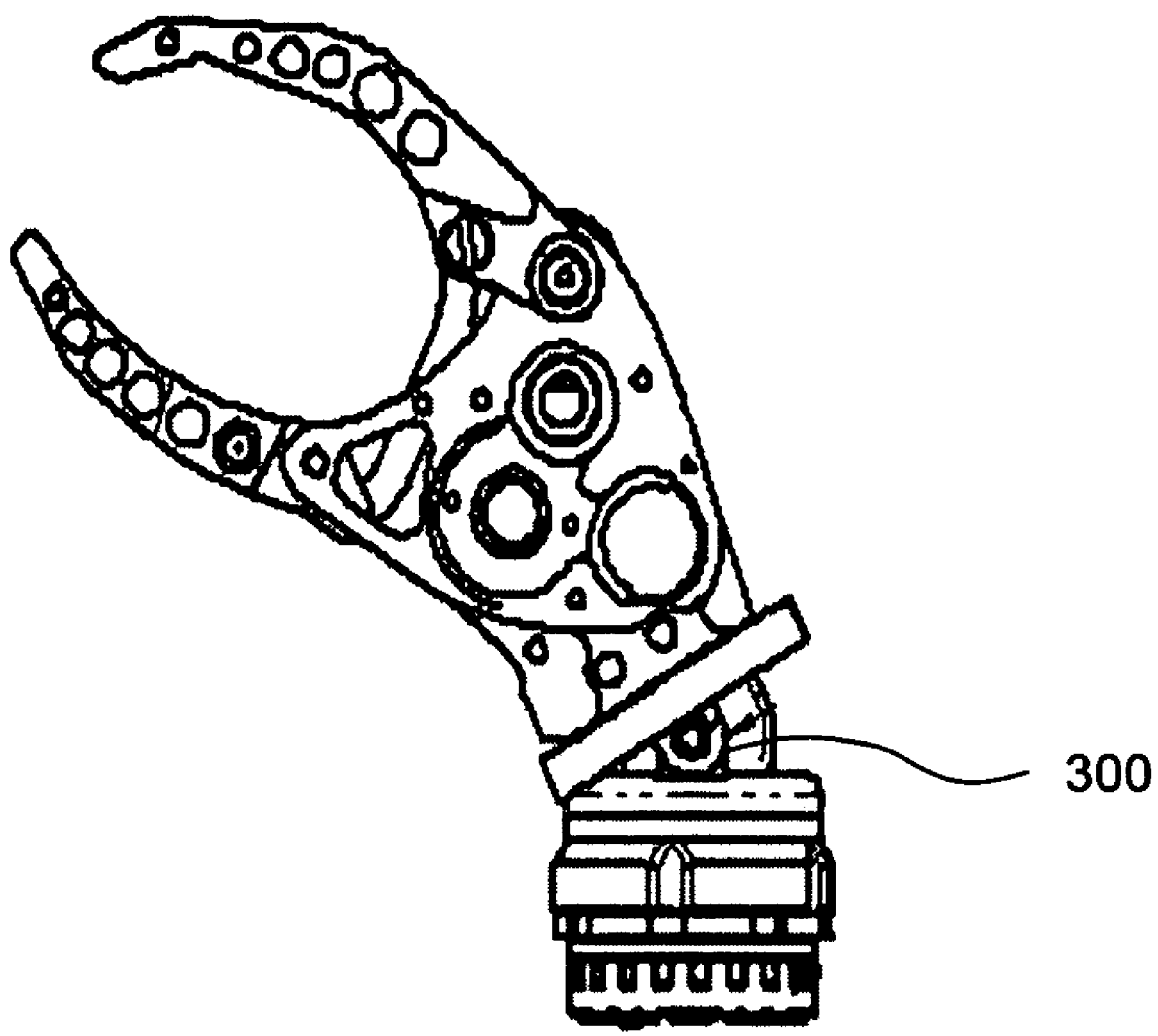
FIG. 7 is a side view of an embodiment of the invention for a prosthetic device with flexion and extension.

FIG. 4, FIG. 5, FIG. 6, and FIG. 7 show an embodiment of the present invention that includes a torsional spring 300 and a locking rotator structure with a sliding lock mechanism and a semi-cylindrical rotator with locking slots. One end of the torsional spring can be coupled to either the base plate 304 or the cover plate 302, and the other end is attached to the upper mounting plate 306. The torsional spring can be configured to allow a locking wrist rotator structure to exhibit compliance in an extension or flexion direction, and then return the wrist device to an upright position. FIG. 4 shows a torsional spring 300 in the present invention in a perspective view. FIG. 5 shows the wrist device held in an upright position, FIG. 6 shows the wrist device rotated in an extension direction, and FIG. 7 shows the wrist device rotated in a flexion direction.

The prosthetic device can also include a secondary latch that holds the sliding lock plate in an unlocked position and allows free compliant flexion and extension movement of the prosthetic limb. The secondary latch can be a ring configured to slide over the sliding lock mechanism, according to one embodiment of the present invention. This secondary latch allows a prosthesis user to grasp objects without loosening their grip when the wrist rotates. For example, the prosthesis user can close a door by grasping the door knob securely with a prosthetic hand, and even while the door swings closed the compliant wrist is passively flexed to allow the grasp to remain secure. The wrist device of the present invention provides a lightweight prosthetic joint that can exhibit compliance in the flexion and extension directions, but the device does not make a prosthetic arm too long to be useful to an amputee.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A wrist device for use with a prosthetic limb, comprising:
    a base plate having an opening, the base plate being configured for attachment to a prosthetic limb;
    a sliding lock plate having an opening, being slidably engaged with the base plate; and
    a semi-cylindrical rotator with slots, wherein the semi-cylindrical rotator is configured for attachment to a prosthetic hand and coupled to the base plate in a manner that allows the sliding lock plate to lock into the slots, and wherein the semi-cylindrical rotator is positioned at least partially in the opening of the base plate and the opening of the sliding lock plate in order to minimize a height of the wrist device.

2. A wrist device for use with a prosthetic limb as in claim 1, further comprising:
    a primary latch return spring coupled between the base plate and the sliding lock plate, wherein the primary latch return spring biases the sliding lock plate in a locked position; and
    a cover plate having an opening configured to receive the semi-cylindrical rotator, the cover plate being coupled to the base plate in a manner that limits movement of the sliding lock plate.

3. A wrist device for use with a prosthetic limb as in claim 1, further comprising:
    two supporting arms attached to the base plate; and
    a pivot pin coupled to the supporting arms of the base plate and the rotator in order to allow rotation of the rotator.

4. A wrist device for use with a prosthetic limb as in claim 1, further comprising an opening in a central portion of the semi-cylindrical rotator.

5. A wrist device for use with a prosthetic limb as claimed in claim 4, further comprising wires routed through the opening in the base plate, the opening in the sliding lock plate, an opening in a cover plate, and the opening in the central portion of the semi-cylindrical rotator.

6. A wrist device for use with a prosthetic limb as claimed in claim 5, wherein the wires are wrapped around a neutral axis in a manner that reduces the effects of repetitive flexing of the wires.

7. A wrist device for use with a prosthetic limb as claimed in claim 5, wherein the wires are multi-strand wires that can withstand repetitive flexing.

8. A wrist device for use with a prosthetic limb as claimed in claim 1, wherein the sliding lock plate extends a full width of the wrist device.

9. A prosthetic device comprising:
    a base plate having an opening, and being configured for attachment to a prosthetic arm;
    a sliding lock plate slidably engaged to the base plate, the sliding lock plate having an opening; and
    a semi-cylindrical rotator with slots, configured to have a rotation axis, perpendicular to an arm axis and configured for attachment to a prosthetic hand, wherein the semi-cylindrical rotator is coupled to the base plate in a manner that allows the sliding lock plate to lock into the slots of the semi-cylindrical rotator, and wherein the semi-cylindrical rotator is positioned at least partially in the opening of the base plate and the opening of the sliding lock plate in order to minimize a height of the wrist device.

10. A prosthetic device as claimed in claim 9, further comprising:
    a lower mounting plate coupled to the base plate;
    a cover plate coupled to the base plate;
    a wrist quick disconnect unit coupled to the lower mounting plate;
    an upper mounting plate coupled to the semi-cylindrical rotator; and
    a mechanical hand coupled to the upper mounting plate.

11. A prosthetic device as claimed in claim 10, further comprising:
    a coax connector coupled to the wrist quick disconnect unit; and
    a bundle of wires coupled to the coax connector and routed through the wrist disconnect unit, the lower mounting plate, the base plate, the sliding lock plate, the semi-cylindrical rotator, the cover plate, and the upper mounting plate, and coupled to the mechanical hand.

12. A prosthetic joint, comprising:
    a base plate configured for attachment to a prosthetic arm;
    a locking rotator structure, wherein the locking rotator structure is rotatably attached to the base plate and includes a sliding lock plate and a semi-cylindrical rotator;
    a prosthetic hand coupled to the semi-cylindrical rotator of the locking rotator structure; and
    a torsional spring coupled to the base plate and to the prosthetic hand in a manner that enables the locking rotator structure to exhibit compliance in a flexion direction and an extension direction.

13. A prosthetic device configured for attachment to an amputee's arm, comprising:
    a prosthetic hand;
    a locking wrist rotator structure, wherein the locking wrist rotator structure includes a sliding lock mechanism and a semi-cylindrical rotator with locking slots configured for engagement with the sliding lock mechanism;
    a torsional spring coupled to the locking wrist rotator structure and to the prosthetic hand in a manner that allows the prosthetic hand to exhibit compliance in a flexion direction and an extension direction.

* * * * *